(12) United States Patent
Adachi et al.

(10) Patent No.: US 8,583,208 B2
(45) Date of Patent: Nov. 12, 2013

(54) SUPERCONDUCTING MAGNETISM MEASURING APPARATUS, BIOMAGNETISM MEASURING APPARATUS, AND SENSOR CYLINDER COVER AND SHEET FOR BIOMAGNETISM MEASURING APPARATUS

(75) Inventors: Yoshiaki Adachi, Tokyo (JP); Shigenori Kawabata, Tokyo (JP); Shoji Tomizawa, Tokyo (JP)

(73) Assignees: University Corporation, Kanazawa Institute of Technology, Ishikawa (JP); National University Corporation, Tokyo Medical and Dental University, Tokyo (JP)

( * ) Notice: Subject to any disclaimer, the term of this patent is extended or adjusted under 35 U.S.C. 154(b) by 1447 days.

(21) Appl. No.: 12/224,249

(22) PCT Filed: Feb. 20, 2007

(86) PCT No.: PCT/JP2007/000103
§ 371 (c)(1),
(2), (4) Date: Aug. 21, 2008

(87) PCT Pub. No.: WO2007/099697
PCT Pub. Date: Sep. 7, 2007

(65) Prior Publication Data
US 2009/0012384 A1    Jan. 8, 2009

(30) Foreign Application Priority Data

Feb. 23, 2006 (JP) .................................. 2006-046176
Feb. 28, 2006 (JP) .................................. 2006-051768

(51) Int. Cl.
*A61B 5/05* (2006.01)

(52) U.S. Cl.
USPC .......................................... 600/409; 600/407

(58) Field of Classification Search
USPC ......................................................... 600/409
See application file for complete search history.

(56) References Cited

U.S. PATENT DOCUMENTS

| 5,617,856 A * | 4/1997 | Tamura et al. ................. 600/409 |
| 6,187,032 B1 * | 2/2001 | Ohyu et al. .................... 600/409 |
| 2004/0193037 A1 * | 9/2004 | Tsukada et al. ............... 600/409 |

FOREIGN PATENT DOCUMENTS

| JP | 2-95336 | 4/1990 |
| JP | 2000-51169 | 2/2000 |
| JP | 2002-57377 | 2/2002 |
| JP | 2005-337862 | 12/2005 |

* cited by examiner

*Primary Examiner* — Unsu Jung
*Assistant Examiner* — Saurel J Selkin
(74) *Attorney, Agent, or Firm* — Jordan and Hamburg LLP

(57) ABSTRACT

Magnetism generated in the cervical or waist part of a subject is measured without the neck or waist of the subject being bent forward. A sensor cylinder is arranged to have a four-sided cylindrical shape. One side at the distal end of the sensor cylinder is moderately curved. This allows the side at the distal end of the sensor cylinder to come into direct contact with the cervical or waist part of the subject when the neck or waist remains not belt forward, whereby a faint magnetism generated in the spinal cords or nerves of the subject can favorably be measured.

21 Claims, 14 Drawing Sheets

Fig. 9  sensor cylinder cover for biomagnetism measurering apparatus
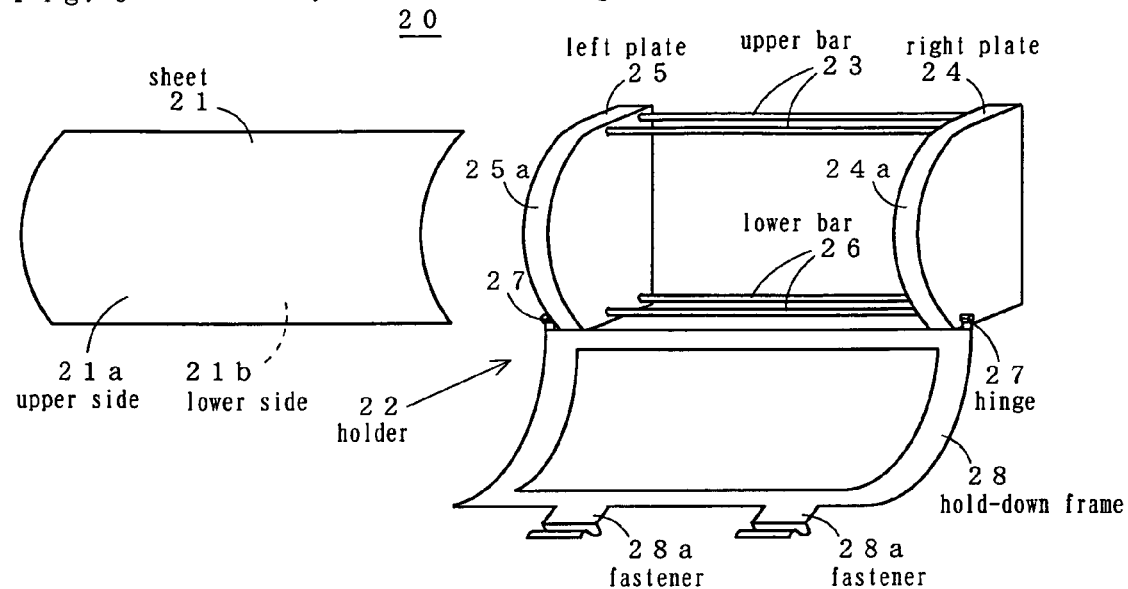
Fig. 10  sensor cylinder cover for biomagnetism measurering apparatus
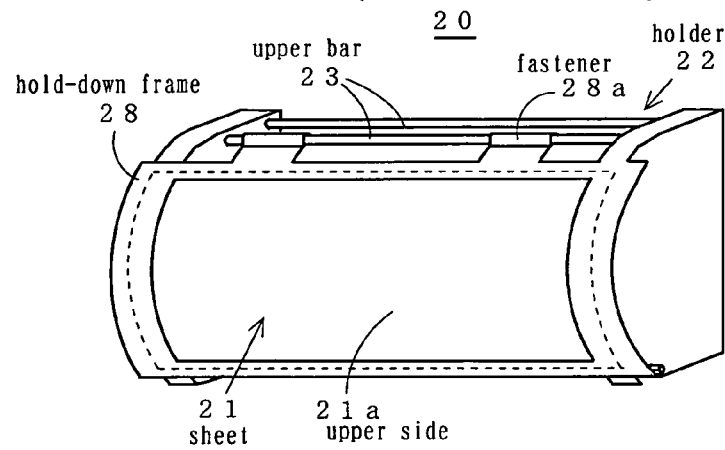

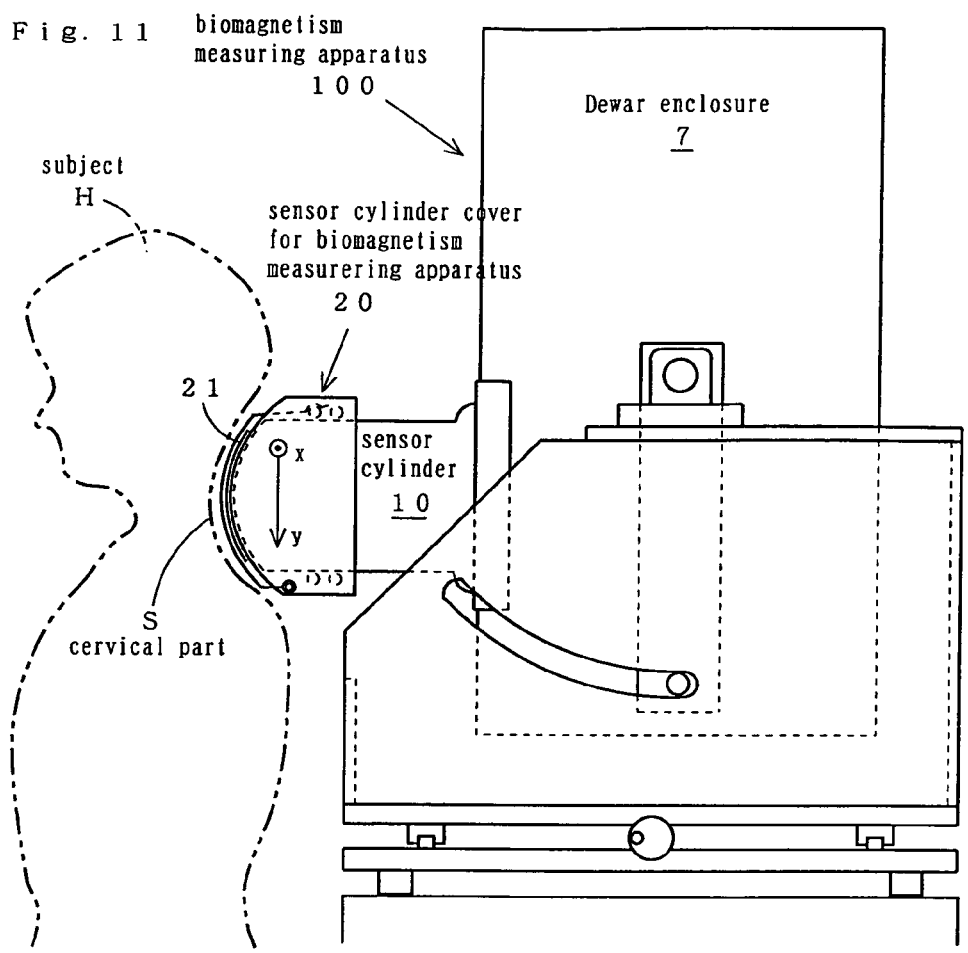
Fig. 11 biomagnetism measuring apparatus 100
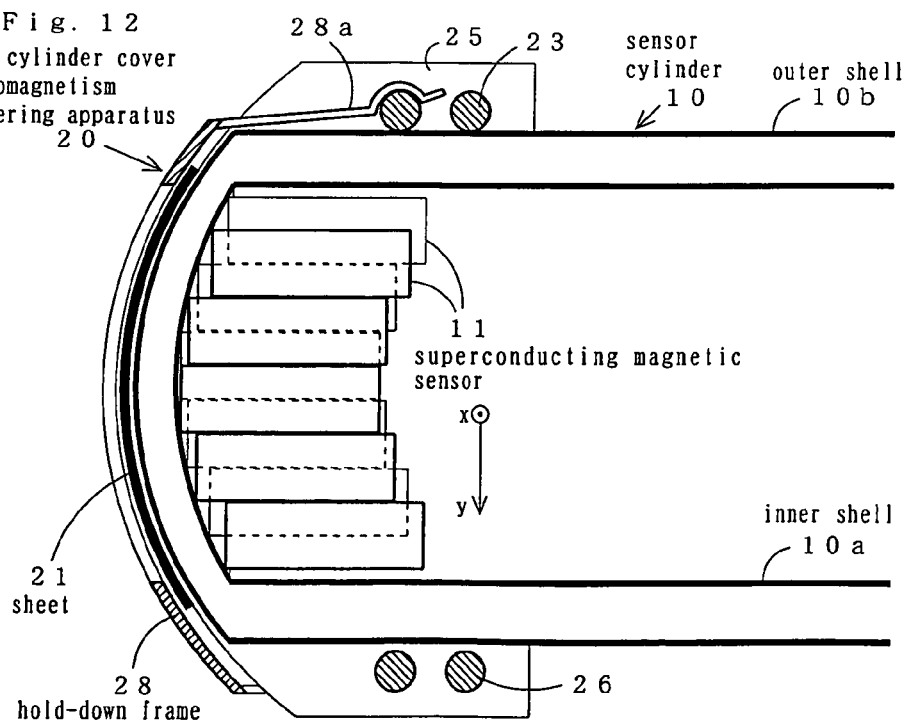
Fig. 12 sensor cylinder cover for biomagnetism measurering apparatus 20

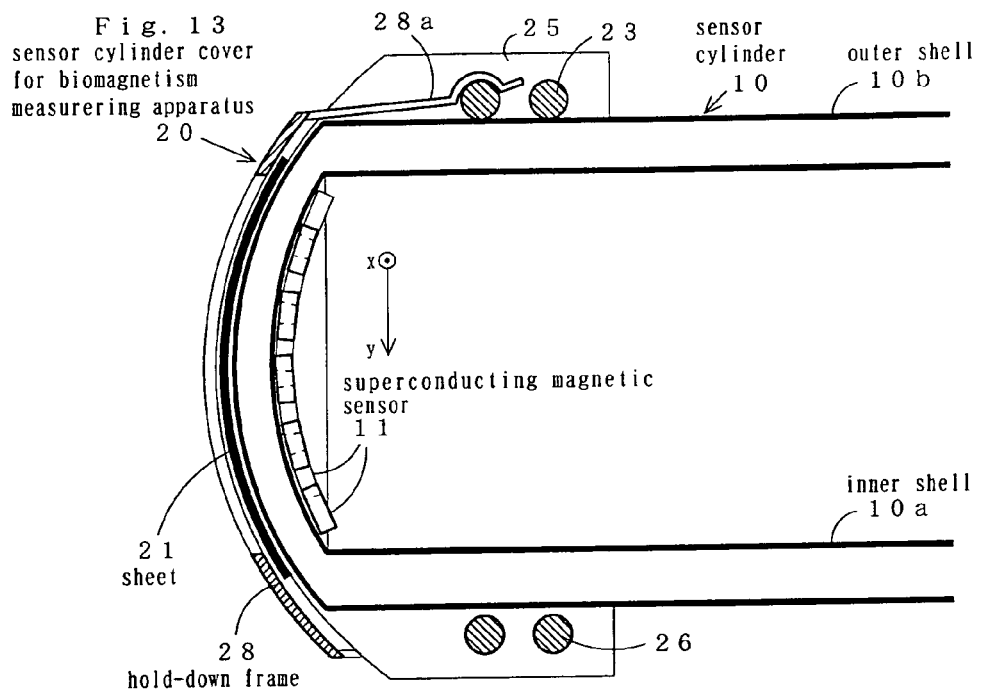
Fig. 13 sensor cylinder cover for biomagnetism measurering apparatus 20
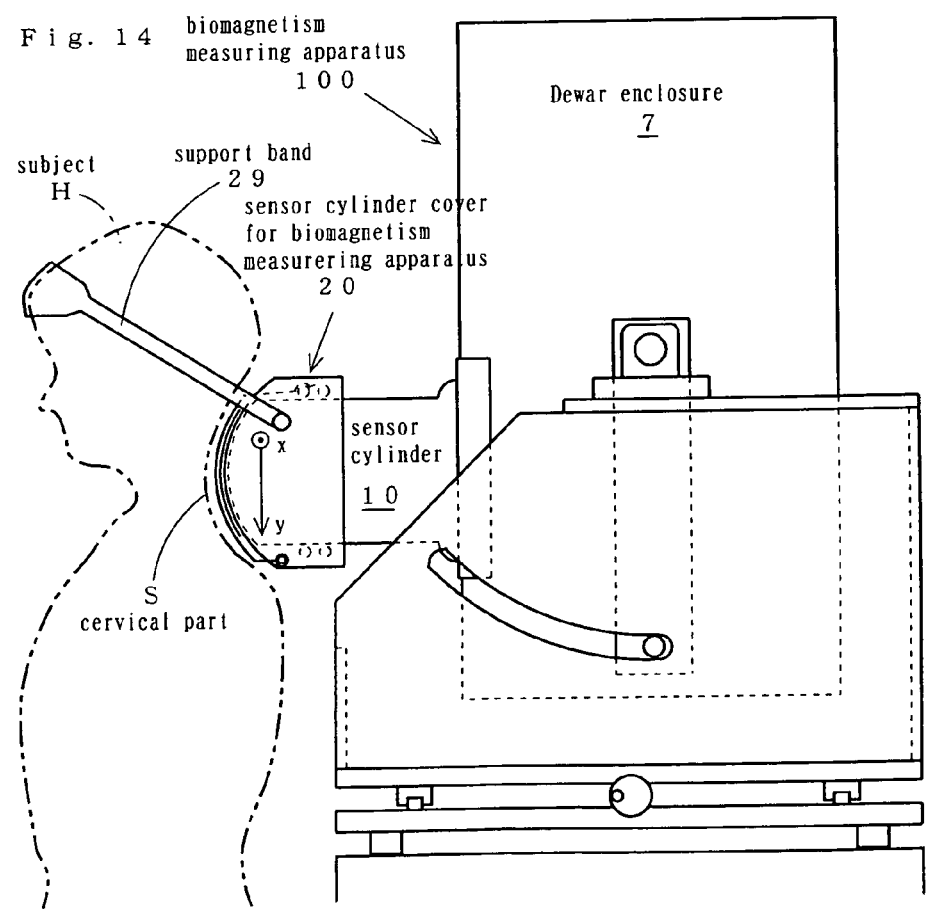
Fig. 14 biomagnetism measuring apparatus 100

Fig. 15 sheet 21
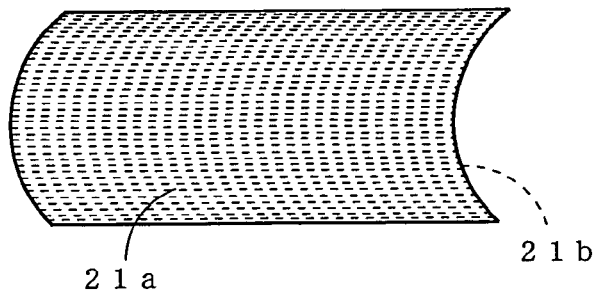
Fig. 16
biomagnetism measuring apparatus 100
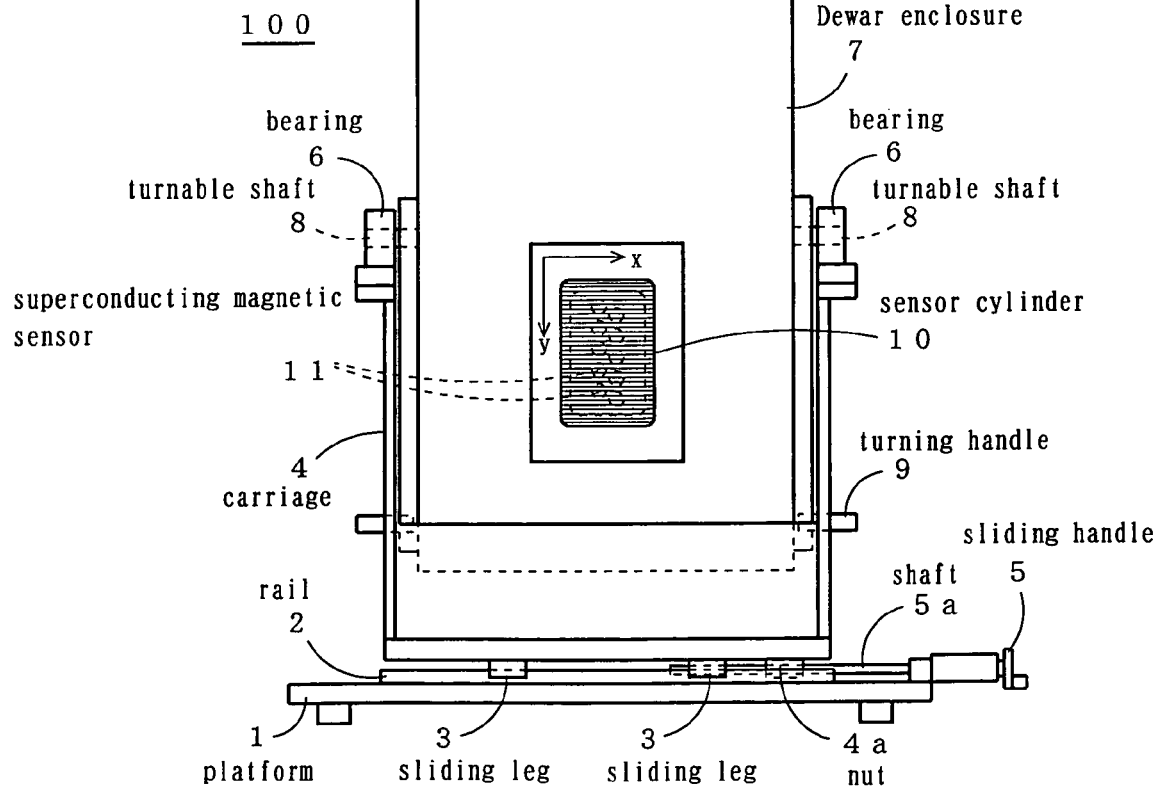

Fig. 17    sensor cylinder
                  10
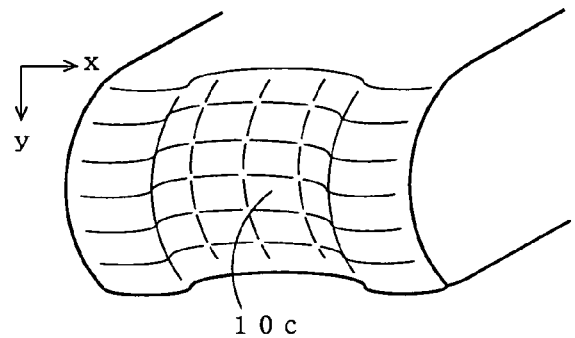
Fig. 18    X ⊙ ⟶ Z    superconducting magnetism measuring apparatus
           ↓                                        100
           Y
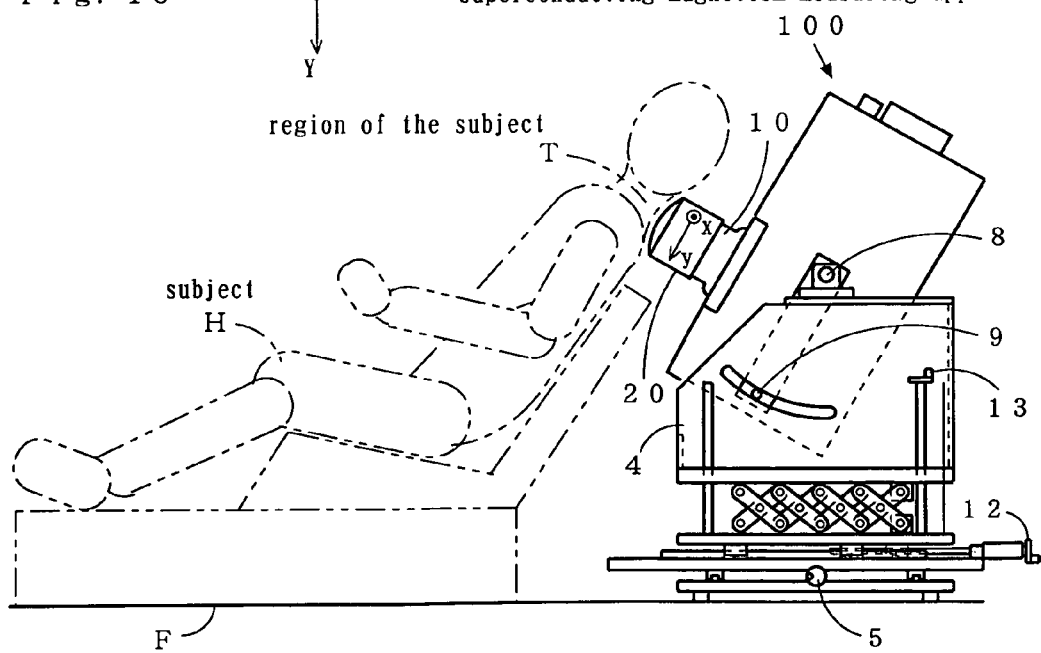

Fig. 23
| model No. | A | B | C | D |
|---|---|---|---|---|
| projection | 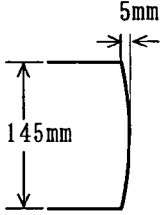 | 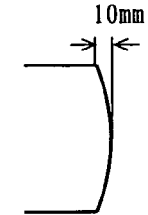 | 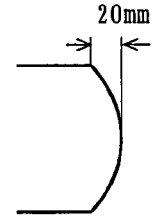 | 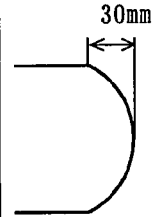 |
| number of the patients matched | 2 | 1 1 | 1 4 | 0 |

SUPERCONDUCTING MAGNETISM MEASURING APPARATUS, BIOMAGNETISM MEASURING APPARATUS, AND SENSOR CYLINDER COVER AND SHEET FOR BIOMAGNETISM MEASURING APPARATUS

FIELD OF THE INVENTION

The present invention relates to a superconducting magnetism measuring apparatus, a biomagnetism measuring method, and a sensor cylinder cover and a sheet for a biomagnetism measuring apparatus and more particularly to a superconducting magnetism measuring apparatus which is capable of measuring a faint degree of magnetism generated in the cervical or waist part of a subject to be measured.

BACKGROUND OF THE INVENTION

A superconducting magnetism measuring apparatus has been known which has an array of superconducting magnetic sensors, where rows of the superconducting magnetic sensors extending along the y direction are dislocated from each other along the x direction, mounted on the inner surface of one side at the distal end of a sensor cylinder (for example, see Patent Citation 1).

The conventional superconducting magnetism measuring apparatus is operated for holding one side at the distal end of the sensor cylinder in direct contact with a living subject to be measured and measuring the biomagnetism in the living subject with the magnetic sensors installed in the sensor cylinder while the sensor cylinder being repeatedly moved in relation to the living subject.

Patent Citation 1: Japanese Patent Laid-open Publication No. 2005-337862.

DISCLOSURE OF THE INVENTION

Problems that the Invention is to Solve

As the side at the distal end of the sensor cylinder in the conventional superconducting magnetism measuring apparatus is arranged of a planer shape, it has to come into direct contact with the cervical part of a subject to be examined while the neck of the subject remains slightly bent forward so that its cervical part extends straight for measurement of a faint magnetism generated in the cervical part. It is equally necessary for measuring a faint magnetism generated in the waist of the subject to hold the side at the distal end of the sensor cylinder in direct contact with the waist of the subject while the waist remains slightly bent forward so that it extends straight.

However, when the subject to be examined is old enough to decrease the flexibility (the movable range) of its spinal column and hardly be bent forward but stay curved naturally at the cervical or waist part, the side at the distal end of the sensor cylinder may fail to come into direct contact with the cervical or waist part of the subject hence permitting the measurement of biomagnetism with much difficulty. Also, when the neck or waist is forcefully bent, its muscles activity creates an unwanted magnetic field which will be a source of noises thus to disturb the measurement of biomagnetism.

Similarly, a conventional biomagnetism measuring apparatus has a sensor cylinder made of a plastic material and arranged smooth at its side at the distal end.

However, when the smooth side at the distal end of the sensor cylinder comes into direct contact with, for example, the skin of the subject to be examined, it sticks to the skin depending on the moisture of the skin and its movement directly on the skin may become difficult.

It is hence an object of the present invention to provide a superconducting magnetism measuring apparatus arranged capable of favorably measuring a faint degree of magnetism generated in the cervical or waist part of a subject to be examined while the neck of the subject remains not bent forward and also to a biomagnetism measuring method, a biomagnetism measuring apparatus, and a sensor cylinder cover and a sheet for the biomagnetism measuring apparatus which allows the sensor cylinder to move smoothly while preventing the side at the distal end of the sensor cylinder remains stuck up to the skin of a subject to be examined.

Means for Solving the Problems

According to a first aspect of the present invention, a superconducting magnetism measuring apparatus having a sensor array of superconducting magnetic sensors aligned and mounted on the inner surface of one side at the distal end of a sensor cylinder thereof is characterized in that the side at the distal end of the sensor cylinder is arranged of an arcuate shaped wall.

In the superconducting magnetism measuring apparatus of the first aspect, the side at the distal end of the sensor cylinder is arranged of an arcuate shape and can thus come into direct contact with the cervical part of a subject to be examined at a degree enough to measure the biomagnetism even when the neck of the subject is not bent forward but remains curved naturally. Equally, the side at the distal end of the sensor cylinder can thus come into direct contact with the waist of a subject to be examined at a degree enough to measure the biomagnetism even when the waist of the subject is not bent forward but remains curved naturally. More specifically, a faint degree of magnetism generated in the spinal cords or nerves of a subject to be examined can be measured without difficulty even when the neck or waist of the subject is not bent forward but remains held naturally.

According to a second aspect of the present invention, the superconducting magnetism measuring apparatus of the first aspect may be modified in which the superconducting magnetic sensors in the sensor array are aligned in the y direction and the x direction while the side at the distal end is moderately curved so as to project outwardly at the center from both the upper and lower ends along the y direction but not curved along the x direction.

In the superconducting magnetism measuring apparatus of the second aspect, the side at the distal end of the sensor cylinder can come into direct contact with the cervical or waist part of a subject to be examined along the y direction even when the neck or waist of the subject is not bent forward but remains curved naturally. As its side at the distal end is not curved along the x direction, the sensor cylinder can be moved along the x direction without being interrupted by the cervical or waist part of the subject.

According to a third aspect of the present invention, the superconducting magnetism measuring apparatus of the second aspect may be modified in which the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is moderately curved so as to project outwardly at the center not smaller than 0.5 cm and not greater than 4 cm from both the upper and lower ends along the y direction.

In the superconducting magnetism measuring apparatus of the third aspect, the side at the distal end of the sensor cylinder can come into direct contact with the cervical or waist part of a subject to be examined along the y direction even when the neck or waist of the subject is not bent forward but remains curved naturally. As its side at the distal end is not curved along the x direction, the sensor cylinder can be moved along the x direction without being interrupted by the cervical or waist part of the subject.

According to a fourth aspect of the present invention, the superconducting magnetism measuring apparatus of the third aspect may be modified in which the sensor cylinder is substantially 145 mm in the width along the y direction and its side at the distal end is moderately curved so as to project outwardly at the center not smaller than 0.5 cm and not greater than 3 cm from both the upper and lower ends along the y direction.

In the superconducting magnetism measuring apparatus of the fourth aspect, the side at the distal end of the sensor cylinder can come into direct contact with the cervical part of a subject to be examined along the y direction even when the neck of the subject is not bent forward but remains curved naturally.

According to a fifth aspect of the present invention, the superconducting magnetism measuring apparatus of the first aspect may be modified in which the superconducting magnetic sensors in the sensor array are aligned in both the y direction and the x direction while the side at the distal end is moderately curved so as to project outwardly at the center from both the upper and lower ends along the y direction and to be recessed at the center from both the upper and lower ends along the x direction.

In the superconducting magnetism measuring apparatus of the fifth aspect, the side at the distal end of the sensor cylinder can come into direct contact with the cervical or waist part of a subject to be examined along the y direction even when the neck or waist of the subject is not bent forward but remains curved naturally. Similarly, the side at the distal end of the sensor cylinder can come into direct contact with the cervical or waist part of the subject along the x direction.

According to a sixth aspect of the present invention, the superconducting magnetism measuring apparatus defined in any of claims 1 to 5 may be modified in which the side at the distal end of the sensor cylinder is provided visibly with markers made of a non-magnetic material which hardly allows X-ray to pass.

In the superconducting magnetism measuring apparatus of the sixth aspect, the location of the markers in relation to the superconducting magnetic sensors is identified from X-ray images of the side at the distal end of the sensor cylinder taken along the x direction by an X-ray photographic action and used for positioning the side at the distal end of the sensor cylinder directly to the neck or waist of the subject, whereby the superconducting magnetic sensors can correctly be positioned in relation to the neck or waist of the subject. The non-magnetic material is utilized for fabricating the markers because it hardly disturbs the measurement of a faint degree of magnetism.

According to a seventh aspect of the present invention, the superconducting magnetism measuring apparatus defined in any of claims 1 to 6 may further comprise an X-ray photographing means for producing X-ray photos of a space along the x direction which includes the side at the distal end of the sensor cylinder.

In the superconducting magnetism measuring apparatus of the seventh aspect, the spinal column of the subject are recorded together with the side at the distal end of the sensor cylinder in an X-ray image taken by the X-ray photographic action with the side at the distal end of the sensor cylinder remaining in direct contact with the neck or waist of the subject, whereby the positional relationship between the spinal column of the subject and the superconducting magnetic sensors aligned along the y direction can be identified. Consequently, it is judged from the comparison between the signals released from the superconducting magnetic sensors where has a defect in the spinal cords and nerves of the subject. For example, when the signal released from the superconducting magnetic sensor allocated close to the fourth cervical vertebra is low, it is judged that the fourth cervical vertebra at higher level has a defect.

According to an eighth aspect of the present invention, the superconducting magnetism measuring apparatus defined in any of claims 1 to 7 may further comprise a leftward/rightward moving means for moving the sensor cylinder along the x direction, a turning means for turning the sensor cylinder about the axis extending along the x direction, a forward/backward moving means for moving the sensor cylinder along the horizontal direction extending perpendicular to the x direction, and an upward/downward moving means for moving the sensor cylinder upwardly and downwardly.

In the superconducting magnetism measuring apparatus of the eighth aspect, the sensor cylinder can favorably be moved three-dimensionally and adjusted in the angle of elevation.

According to a ninth aspect of the present invention, a biomagnetism measuring method is provided comprising the steps of holding horizontally the sensor cylinder of the superconducting magnetism measuring apparatus of the eighth aspect and moving its side at the distal end from the back to a living subject to be measured, allowing the side at the distal end of the sensor cylinder (or when the sensor cylinder is protected with a sensor cylinder cover, one side at the distal end of the sensor cylinder cover) to come partially into direct contact with a region of the living subject, and turning the side at the distal end of the sensor cylinder about the contact until the side at the distal end of the sensor cylinder (or the side at the distal end of the sensor cylinder cover) comes entirely into direct contact with the region of the living subject.

In the superconducting magnetism measuring method of the ninth aspect, the side at the distal end of the sensor cylinder (or when the sensor cylinder is protected with a sensor cylinder cover, one side at the distal end of the sensor cylinder cover) is not slid directly on the subject to be measured, hence preventing the subject from receiving any uncomfortable feeling.

As a tenth aspect of the present invention, a biomagnetism measuring method is provided comprising the steps of allowing the side at the distal end of the sensor cylinder (or when the sensor cylinder is protected with a sensor cylinder cover, one side at the distal end of the sensor cylinder cover) of the superconducting magnetism measuring apparatus defined in claim 8 to come entirely into direct contact with a region of the living subject, turning the side at the distal end of the sensor cylinder about the center of curvature of the arcuate shape of the side at the distal end of the sensor cylinder, and moving the side at the distal end of the sensor cylinder along the region of a curved form of the living subject.

In the superconducting magnetism measuring method of the tenth aspect, the side at the distal end of the sensor cylinder can be moved along the arcuate surface of a region to be measured.

According to an eleventh aspect of the present invention, a biomagnetism measuring method is provided as characterized by, with a biomagnetism measuring apparatus (100) designed for repeatedly moving its sensor cylinder (10) in relation to a living subject (H) to be measured so as to measure a degree of biomagnetism with an array of magnetic sensors

(11) installed in the sensor cylinder (10) while one side at the distal end of the sensor cylinder (10) moving directly on the living subject (H), a sheet (21) having a back side (21b) thereof arranged for producing smoothness against the side at the distal end of the sensor cylinder (10) and a front side (10a) thereof arranged for not producing smoothness against the living subject (H) and disposed between the side at the distal end of the sensor cylinder (10) and the living subject (H).

In the biomagnetism measuring method of the eleventh aspect, the sheet (21) is sandwiched between the side at the distal end of the sensor cylinder (10) and the living subject (H). The sheet (21) produces smoothness at its back side (21a) against the side at the distal end of the sensor cylinder (10) but not at its front side (21b) against the living subject (H). As the result, the side at the distal end of the sensor cylinder (10) can move smoothly on the back side (21b) of the sheet (21) without stuck up while the living subject (H) remains stuck up with the sheet (21).

According to a twelfth aspect of the present invention, a sensor cylinder cover (20) for a biomagnetism measuring apparatus is provided comprising, in the biomagnetism measuring apparatus (100) designed for repeatedly moving its sensor cylinder (10) in relation to a living subject (H) to be measured so as to measure a degree of biomagnetism with an array of magnetic sensors (11) installed in the sensor cylinder (10) while one side at the distal end of the sensor cylinder (10) moving directly on the living subject (H), a holder (22) mounted on the side at the distal end of the sensor cylinder (10) for movement in the horizontal direction but not in the vertical direction, and a sheet (21) having a back side (21b) thereof arranged for producing smoothness against the side at the distal end of the sensor cylinder (10) and a front side (10a) thereof arranged for not producing smoothness against the living subject (H) and held by the holder (22).

The sensor cylinder cover (20) for a biomagnetism measuring apparatus of the twelfth aspect allows the sheet (21) to be sandwiched between the side at the distal end of the sensor cylinder (10) and the living subject (H) when the side at the distal end of the sensor cylinder (10) has been covered with the holder (22) and cane into direct contact with the living subject (H). The sheet (21) produces smoothness at its back side (21a) against the side at the distal end of the sensor cylinder (10) but not at its front side (21b) against the living subject (H). As the result, the side at the distal end of the sensor cylinder (10) can move smoothly along the horizontal direction on the back side (21b) of the sheet (21) without stuck up while the living subject (H) remains stuck up with the sheet (21). Meanwhile, with the holder (22) remaining not moved along the vertical direction, the side at the distal end of the sensor cylinder (10) can be inhibited from moving along the vertical direction on the living subject (H). In other words, the side at the distal end of the sensor cylinder (10) can smoothly move only along the horizontal direction.

Moreover, since the sheet (21) is secured by the holder (22), it can be prevented from wrinkling or deforming. The sheet (21) which comes into direct contact with the living subject (H) can be replaced with a new one, thus providing a sanitary advantage.

According to a thirteenth aspect of the present invention, the sensor cylinder cover (20) for a biomagnetism measuring apparatus of the twelfth aspect may be modified in which the sheet (21) has a multiplicity of horizontally extending linear lands and pits provided on the back side (21b) thereof while its front side (21a) remains smooth.

With the sensor cylinder cover (20) for a biomagnetism measuring apparatus of the thirteenth aspect where the sheet (21) has a multiplicity of horizontally extending linear lands and pits provided on the back side (21b) thereof, the side at the distal end of the sensor cylinder (10) can hardly move along the vertical direction on the sheet (21). In other words, the side at the distal end of the sensor cylinder (10) can move smoothly only along the horizontal direction.

According to a fourteenth aspect of the present invention, the sensor cylinder cover (20) for a biomagnetism measuring apparatus of the twelfth or thirteenth aspect may be modified further comprising a fitting member (29) for integrally fitting the holder (22) to the living subject (H).

The sensor cylinder cover (20) for a biomagnetism measuring apparatus of the fourteenth aspect allows the holder (22) to be fitted integral with the living subject (H) by the fitting member (29), thus stabilizing the positional relationship through the holder (22) between the sensor cylinder (10) and the living subject (H).

According to a fifteenth aspect of the present invention, a sheet (21) disposed between a living subject (H) and one side at the distal end (10c) of the sensor cylinder (10) in a biomagnetism measuring apparatus (100) designed for repeatedly moving the sensor cylinder (10) in relation to the living subject (H) to be measured so as to measure a degree of biomagnetism with an array of magnetic sensors (11) installed in the sensor cylinder (10) while the side at the distal end of the sensor cylinder (10) moving directly on the living subject (H) is provided as characterized in that the sheet (21) has a back side (21b) thereof arranged for producing smoothness against the side at the distal end (10c) of the sensor cylinder (10) and a front side (10a) thereof arranged for not producing smoothness against the living subject (H).

The sheet (21) of the fifteenth aspect produces smoothness at its back side (21a) against the side at the distal end of the sensor cylinder (10) but not at its front side (21b) against the living subject (H). As the result, the side at the distal end of the sensor cylinder (10) can move smoothly on the back side (21b) of the sheet (21) without stuck up while the living subject (H) remains stuck up with the sheet (21).

According to a sixteenth aspect of the present invention, the sheet (21) of the fifteenth aspect may be modified in which the sheet (21) has a multiplicity of parallelly extending linear lands and pits provided on the back side (21b) thereof while its front side (21a) remains smooth.

Since the sheet (21) of the sixteenth aspect has a multiplicity of parallelly extending linear lands and pits provided on the back side (21b) thereof, the side at the distal end of the sensor cylinder (10) can hardly move along the direction orthogonal to the linear lands and pits on the sheet (21). In other words, the side at the distal end of the sensor cylinder (10) can move smoothly along the direction of the linear lands and pits.

According to a seventeenth aspect of the present invention, a biomagnetism measuring apparatus (100) designed for repeatedly moving its sensor cylinder (10) in relation to a living subject (H) to be measured so as to measure a degree of biomagnetism with an array of magnetic sensors (11) installed in the sensor cylinder (10) while one side at the distal end of the sensor cylinder (10) moving directly on the living subject (H) is provided as characterized in that the side at the distal end of the sensor cylinder (10) has a multiplicity of horizontally extending linear lands and pits provided thereon.

In the biomagnetism measuring apparatus (100) of the seventeenth aspect, the side at the distal end of the sensor cylinder (10) has a multiplicity of horizontally extending linear lands and pits provided thereon and can thus hardly move along the vertical direction on the sheet (21). In other words, the side at the distal end of the sensor cylinder (10) can smoothly move only along the horizontal direction.

Advantage of the Invention

The superconducting magnetism measuring apparatus according to the present invention can favorably measure a faint degree of magnetism generated in the spinal cords or nerves of a subject to be examined.

BRIEF DESCRIPTION OF THE DRAWINGS

FIG. 9 is an exploded perspective view of a sensor cylinder cover for a biomagnetism measuring apparatus showing Embodiment 3 of the present invention;

FIG. 10 is a perspective view showing the sensor cylinder cover for a biomagnetism measuring apparatus of Embodiment 3;

FIG. 11 is a right side view of the biomagnetism measuring apparatus equipped with the sensor cylinder cover of Embodiment 3;

FIG. 12 is a cross sectional view of the sensor cylinder protected with the sensor cylinder cover for a biomagnetism measuring apparatus of Embodiment 3;

FIG. 13 is a cross sectional view of a sensor cylinder protected with a sensor cylinder cover for a biomagnetism measuring apparatus according to Embodiment 4 of the present invention;

FIG. 14 is a right side view of a biomagnetism measuring apparatus equipped with a sensor cylinder cover for a biomagnetism measuring apparatus according to Embodiment 5 of the present invention;

FIG. 15 is a perspective view of a sheet showing Embodiment 6 of the present invention;

FIG. 16 is a front view of a biomagnetism measuring apparatus showing Embodiment 7 of the present invention;

FIG. 17 is a front view of a biomagnetism measuring apparatus showing Embodiment 8 of the present invention;

FIG. 18 is a right side view of a biomagnetism measuring apparatus showing Embodiment 10 of the present invention;

FIG. 23 is an explanatory view of a sensor cylinder used in Example 1.

DESCRIPTION OF THE NUMERALS

4a: nut, 5a: shaft, 10: sensor cylinder, 10c: one side at the distal end, 11: superconducting magnetic sensor, 100: superconducting magnetism measuring apparatus.

BEST MODES FOR EMBODYING THE INVENTION

The present invention will be described in more detail referring to some embodiments shown in the relevant drawings. It would be understood that the present invention is not limited to the embodiments.

Embodiment 1

Figure 1:
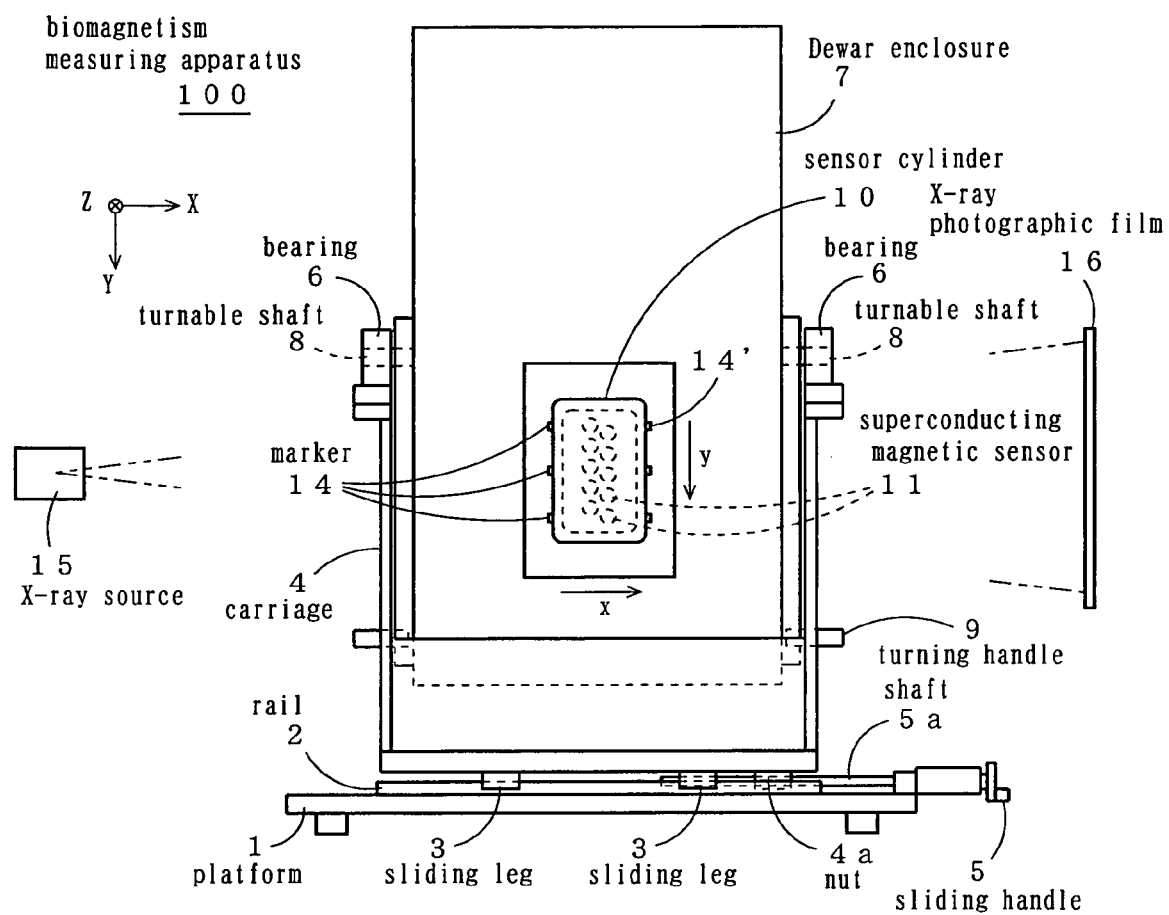
FIG. 1 is a front view of a superconducting magnetism measuring apparatus showing Embodiment 1 of the present invention.

FIG. 1 is a front view of a superconducting magnetism measuring apparatus 100 showing Embodiment 1 of the present invention. The superconducting magnetism measuring apparatus 100 comprises a platform 1 on the upper side of which rails 2 are mounted, a carriage 4 having sliding legs 3 provided for sliding on the rails 2, a sliding handle 5 arranged to be operated by an operator for slidably moving the carriage 4 to the left and the right, bearings 6 mounted to the upper ends of the carriage 4, a Dewar enclosure 7 pivotably supported by a turnable shaft 8 between the bearings 6 and arranged in which a coolant such as liquid helium is stored, a sensor cylinder 10 projectingly mounted on the Dewar enclosure 7, a turning handle 9 arranged to be operated by the operator for tilting the sensor cylinder 10, and an array of superconducting magnetic sensors 11 mounted along the x and y directions on the inner surface of one side at the distal end of the sensor cylinder 10.

It is assumed that the X direction extends from left to right, the Y direction extends from upper to lower, and the Z direction extends from front to rear in a three-dimensional space. When the sensor cylinder 10 extends horizontally, its y direction is equal to the X direction.

Also, markers 14, 14' which are made of a non-magnetic hardly allowing X-ray to pass are mounted on both the left and right sides at the distal end of the sensor cylinder 10. More particularly, the markers 14, 14' are implemented by, for example, titanium or brass screws. The markers 14 on the left side are arranged of a four sided shape while the markers 14' on the right side are arranged of a round shape.

The superconducting magnetism measuring apparatus 100 includes an X-ray source 15 and an X-ray photographic film 16 for producing X-ray photos along the x direction of the space including the distal end of the sensor cylinder 10.

Figure 2:
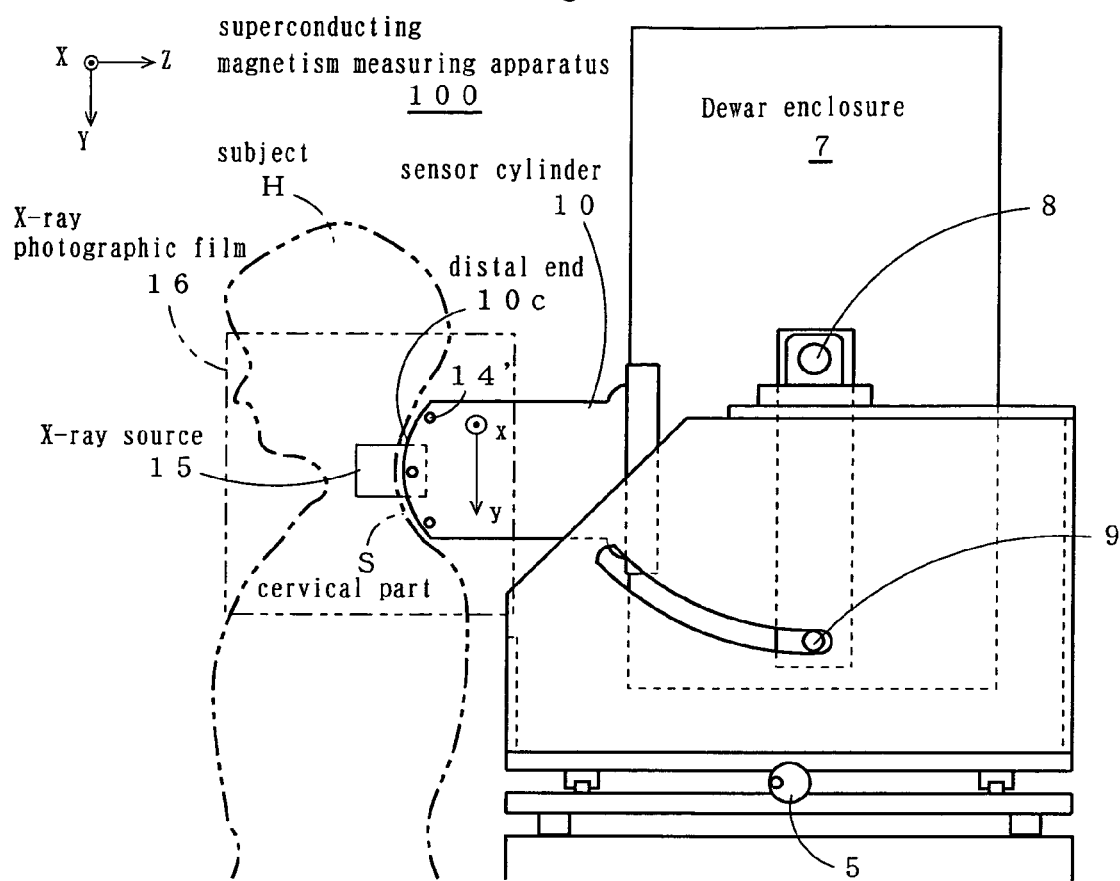
FIG. 2 is a right side view of the superconducting magnetism measuring apparatus of Embodiment 1.

FIG. 2 is a right side view of the superconducting magnetism measuring apparatus 100.

The sensor cylinder 10 is arranged of a four sided shape which is greater than 5 cm and smaller than 20 cm in the width along the y direction and greater than 5 cm and smaller than 20 cm in the width along the x direction. One side at the distal end 10c of the sensor cylinder 10 is curved along the y direction to project outwardly at the center substantially 0.5 to 4 cm greater than both the upper and lower ends but remains not curved along the x direction. Preferably, the width along the y direction of the sensor cylinder 10 is substantially 145 mm while the center of the side at the distal end 10c projects greater than 0.5 cm and smaller than 3 cm along the y direction from both the upper and lower ends to form a smooth curved surface with no curve along the x direction.

Figure 3:
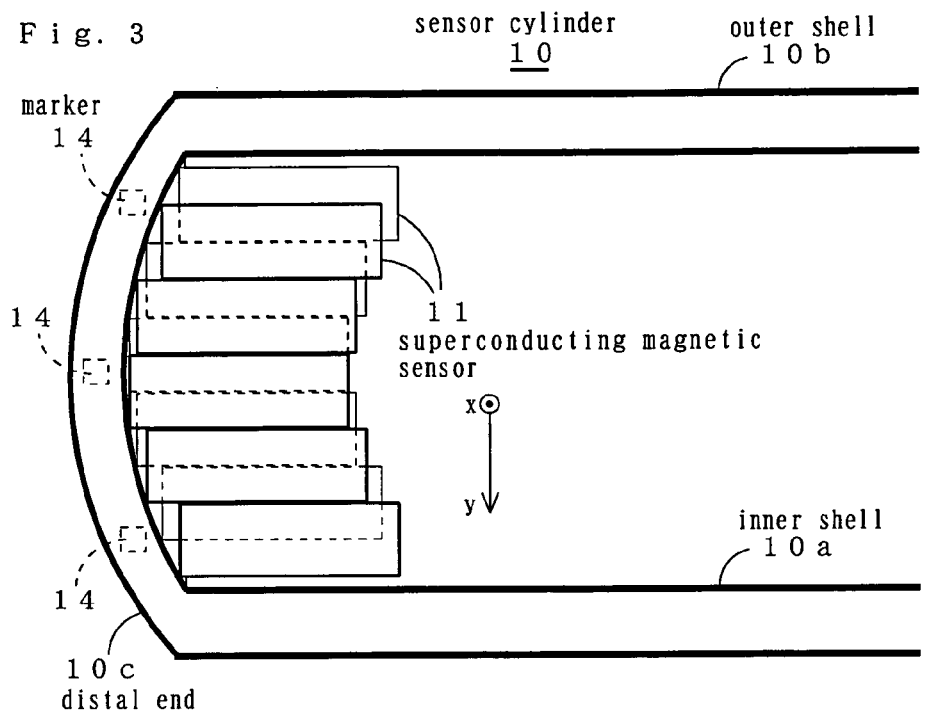
FIG. 3 is a cross sectional view of a sensor cylinder in the superconducting magnetism measuring apparatus of Embodiment 1.

FIG. 3 is a cross sectional view showing the interior of the side at the distal end 10c of the sensor cylinder 10.

The sensor cylinder 10 comprises an inner shell 10a and an outer shell 10b. The superconducting magnetic sensors 11 are disposed at the inner side of the inner shell 10a.

Figure 4:
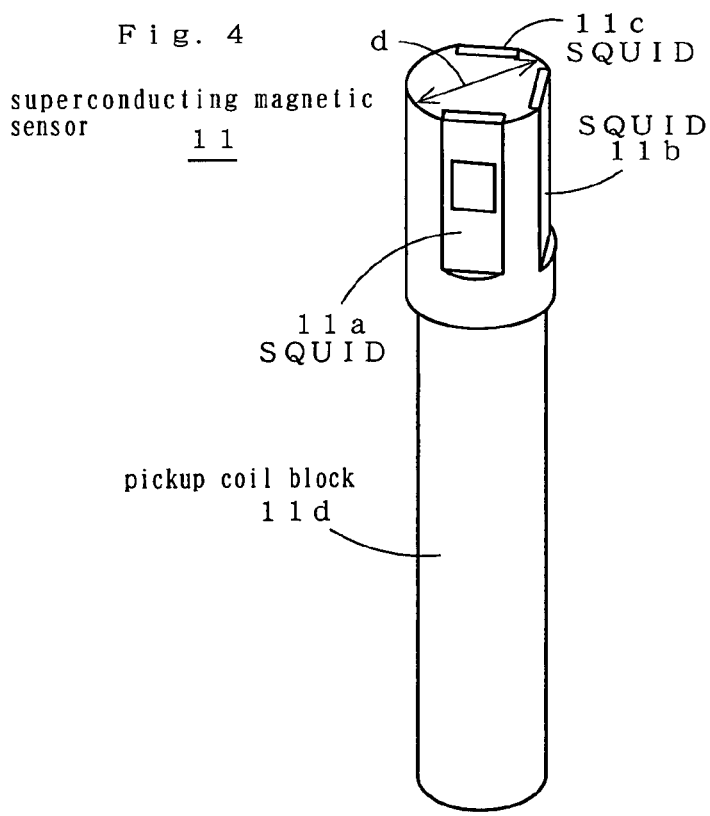
FIG. 4 is a perspective view showing one example of a superconducting magnetic sensor.

FIG. 4 is a perspective view of the superconducting magnetic sensor 11.

The superconducting magnetic sensor 11 incorporates a combination of a cylindrical block of a glass epoxy material having a diameter d (for example, 20 mm) and is equipped with SQUIDs 11a, 11b, 11c and a pickup coil block 11d arranged of a cylindrical shape and joined to the cylindrical block.

Figure 5:
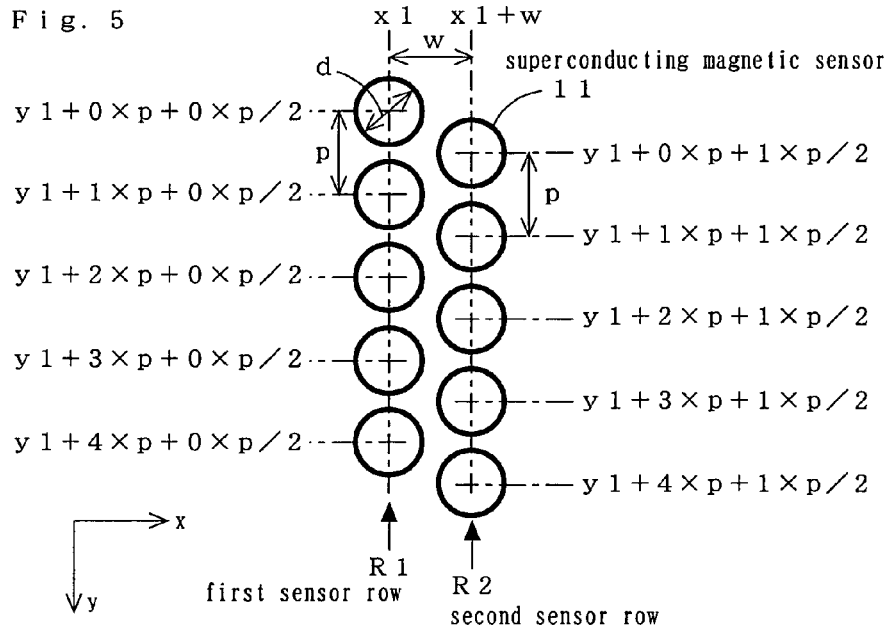
FIG. 5 is a schematic view showing an array of the superconducting magnetic sensors in the superconducting magnetism measuring apparatus of Embodiment 1.

FIG. 5 is a schematic view showing an array of the superconducting magnetic sensors 11.

A first sensor row R1 consists of five superconducting magnetic sensors 11 aligned at intervals of a pitch p (for example, 20 mm) in a row along the y direction.

A second sensor row R2 is spaced by a pitch w (for example, 20 mm) along the x direction from the first sensor row R1 and consists of five superconducting magnetic sensors 11 aligned at intervals of the pitch p in a row along the y direction while its five superconducting magnetic sensors 11 are dislocated by p/2 from the superconducting magnetic sensors 11 of the first sensor row R1 part.

Figure 6:
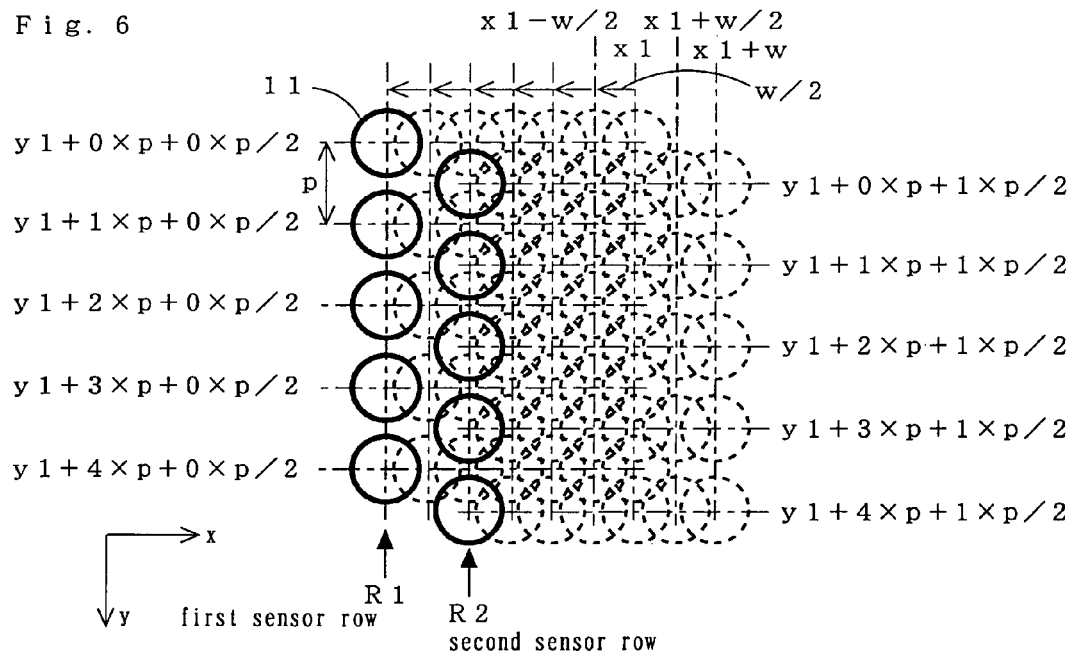
FIG. 6 is a schematic view showing a distribution of measuring points in the superconducting magnetism measuring apparatus of Embodiment 1.

FIG. 6 illustrates a density profile of measuring points where after the first measurement, the second measurement is carried out with the carriage 4 slidably moved by w/2 along the x direction from its initial location, the third measurement is carried out with the carriage 4 slidably moved further by w/2 along the x direction, the fourth measurement is carried out with the carriage 4 slidably moved further by w/2 along the x direction, the fifth measurement is carried out with the carriage 4 slidably moved further by w/2 along the x direction, the sixth measurement is carried out with the carriage 4 slidably moved further by w/2 along the x direction, and the seventh measurement is carried out with the carriage 4 slidably moved further by w/2 along the x direction. More particularly, the pitch along the y direction between the measuring points is equal to the pitch p along the y direction between the superconducting magnetic sensors 11 at both ends of the range of the sliding movement while the pitch along the y direction between the measuring points is equal to ½ the pitch p along the y direction between the superconducting magnetic sensors 11 at the center along the y direction of the range of the sliding movement.

Also, the pitch along the x direction between the measuring points is equal to ½ the pitch w between the sensor rows.

Figure 7:
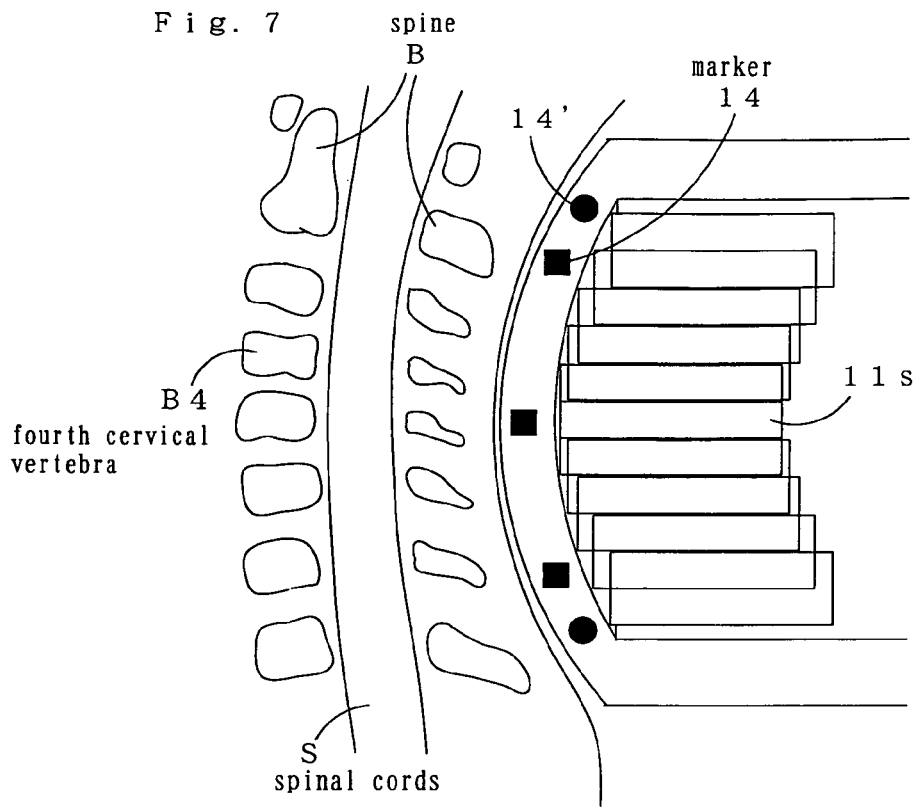
FIG. 7 is a schematic view showing an X-ray image produced in the superconducting magnetism measuring apparatus of Embodiment 1.

FIG. 7 is a schematic view showing an X-ray photograph image taken at the state of FIG. 2.

From the X-ray photograph image, the position along the y direction of the markers 14, 14' relative to the superconducting magnetic sensors 11 can be acknowledged. In other words, the location of the superconducting magnetic sensors 11 relative to the neck or waist of a subject H to be examined can favorably be determined when the side at the distal end of the sensor cylinder 10 has been set directly on the neck or waist of the subject H with reference to the markers 14, 14'.

Moreover, as the relationship between the spine of the subject H and each of the superconducting magnetic sensors 11 remains uniform, the location of the superconducting magnetic sensors 11 relative to the neck or waist of the subject H relative to the superconducting sensors 11 can be acknowledged. For example, when the signal produced by the superconducting magnetic sensor 11s located at the center along the y direction is anomalous, the fourth cervical vertebra S4 at higher position of the spinal cords or nerves located close to the superconducting magnetic sensor 11s has a defect. It is thus satisfied to cut and treat a region about the fourth cervical vertebra S4 when it has been judged that the fourth cervical vertebra S4 has a defect. Since the conventional action of cutting an extended region from the second cervical vertebra to the seventh cervical vertebra is not needed, the stress on a patient can be eased.

The superconducting magnetism measuring apparatus 100 of Embodiment 1 allows the array of the superconducting magnetic sensors 11 to be operated at a higher density for the measuring points than for their original arrangement. Since the array of the sensors are moved only in the x direction, their physical arrangement remains not complicated and their measuring action can be minimized in the number of repeats.

Also, even when the cervical part at the neck of the subject H to be examined remains naturally curved with the neck not tilted forward, it can closely come into direct contact with the side at the distal end 10c of the sensor cylinder 10 along the y direction. Moreover, as its side at the distal end 10c remains not curved along the x direction, the sensor cylinder 10 can be moved along the x direction without being disturbed by the cervical part of the subject H.

Similarly, even when the waist of the subject H remains naturally curved but not tilted forward, it can closely come into direct contact with the side at the distal end 10c of the sensor cylinder 10 along the y direction.

Embodiment 2

Figure 8:
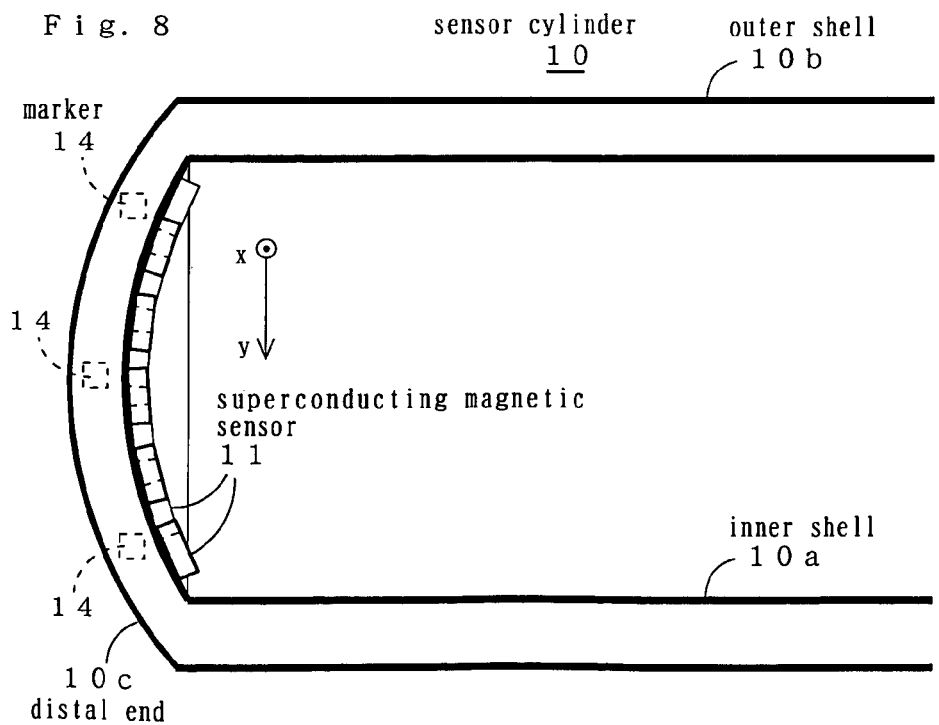
FIG. 8 is a cross sectional view of the sensor cylinder of a superconducting magnetism measuring apparatus showing Embodiment 2 of the present invention.

As shown in FIG. 8, the superconducting magnetic sensors 11 of the cylindrical shape (See FIG. 4) may be replaced by superconducting magnetic sensors of a flat type.

Embodiment 3

FIG. 9 is an exploded perspective view of a sensor cylinder cover 20 for a biomagnetism measuring apparatus showing Embodiment 3 of the present invention.

The sensor cylinder cover 20 for a biomagnetism measuring apparatus comprises a sheet 21 and a holder 22.

The sheet 21 is a plastic sheet of which the upper side 21a and the lower side 21b are finished with smoothness.

The holder 22 comprises upper bars 23, a right plate 24 provided at the right end of the upper bars 23, a left plate 25 provided at the left end of the upper bars 23, lower bars 26 provided to join at the lower between the right plate 25 and the left plate 26, and a hold-down frame 28 pivotably joint by hinges to the right plate 24 and the left plate 25.

The distance between the upper bars 23 and the lower bars 26 is set greater by a few millimeters than the height of the sensor cylinder 10 of a biomagnetism measuring apparatus 100.

The distance between the right plate 24 and the left plate 25 is set greater by 2 cm to 8 cm from the width of the sensor cylinder 10 of the biomagnetism measuring apparatus 100.

The depth of the right plate 24 and the left plate 25 is set smaller by a few centimeters from the length of the sensor cylinder 10 of the biomagnetism measuring apparatus 100.

The front side 24a of the right plate 24 and the front side 25a of the left plate 25 are shaped so as to match the shape at the distal end of the sensor cylinder 10 of the biomagnetism measuring apparatus 100.

As shown in FIG. 10, the sheet 21 is sandwiched between the hold-down frame 28 and the front ends 24a, 25a of the right and left plates 24, 25 and the hold-down frame 28 is fastened at its fastener 28a to the upper bar 23. This permits the sheet 21 to be shaped to match the shape at the distal end of the sensor cylinder 10 of the biomagnetism measuring apparatus 100.

When the side at the distal end 10c of the sensor cylinder 10 comes into direct contact with the skin of a subject H to be examined as shown in FIG. 2, it may stick to the skin due to the moisture of the skin thus disturbing the smooth movement of the sensor cylinder 10.

For compensation, the side at the distal end 10c of the sensor cylinder 10 is protected with the sensor cylinder cover 20 as shown in FIG. 11.

More specifically, the side at the distal end 10c of the sensor cylinder 10 and the skin of the subject H are separated from each other by the sheet 21. Since the back side 21b of the sheet 21 is smoothed, it ensures smoothness on the side at the distal end of the sensor cylinder 10 which is also smoothed. Additionally, the front side 21a of the sheet 21 is smoothed and it can hardly stick to the skin of the subject H regardless of the moisture of the skin. This allows the side at the distal end of the sensor cylinder 10 to smoothly move along the x direction (the horizontal direction) directly on the back side 21b of the sheet 21. Meanwhile, with the holder 22 remaining not moved vertically, the side at the distal end of the sensor cylinder 10 is held not to move along the y direction (the vertical direction).

FIG. 12 is a cross sectional view of the side at the distal end 10c of the sensor cylinder 10 protected with the sensor cylinder cover 20 for the biomagnetism measuring apparatus.

The sensor cylinder 10 comprises an inner shell 10a and an outer shell 10b. An array of superconducting magnetic sensors 11 are mounted on the inner side of the inner shell 10a.

According to Embodiment 3, the biomagnetism measuring method, the sensor cylinder cover 20 for a biomagnetism measuring apparatus, the sheet 21, and the biomagnetism measuring apparatus 100 allow the sensor cylinder 10 to smoothly move along the x direction (the horizontal direction) but not along the y direction (the vertical direction).

Embodiment 4

As shown in FIG. 13, the superconducting magnetic sensors 11 of the cylindrical shape (See FIG. 4) may be replaced by superconducting magnetic sensors of a flat type.

Embodiment 5

As shown in FIG. 14, the holder 22 may be equipped with a rubber support band 29 for being securely joined to the subject H with the help of the support band 29.

Since the holder 22 is securely joined to the subject H, the positional relationship through the holder 22 between the subject H and the sensor cylinder 10 can be held at stability.

Embodiment 6

As shown in FIG. 15, the sheet 21 may have a multiplicity of horizontally extending linear lands and pits provided on the back side 21b.

With the horizontally extending linear lands and pits provided on its back side 21b, the sheet 21 prevents the side at the distal end of the sensor cylinder 10 from slidably moving in the vertical to the sheet 21. More particularly, the side at the distal end of the sensor cylinder 10 can smoothly move only along the horizontal direction.

Embodiment 7

As shown in FIG. 16, the sensor cylinder 10 of the biomagnetism measuring apparatus 100 may have a multiplicity of horizontally extending linear lands and pits provided on its side at the distal end.

With the horizontally extending linear lands and pits provided on its side at the distal end, the sensor cylinder 10 is prevented from slidably moving in the vertical to the sheet 21. More particularly, the side at the distal end of the sensor cylinder 10 can smoothly moved only along the horizontal direction.

Embodiment 8

The sheet 21 may be fastened to the holder 22 by screws or an area fastener(s).

Embodiment 9

As shown in FIG. 17, the side at the distal end 10c of the sensor cylinder 10 may have a saddle-shaped arcuate surface thereof provided which is bulged more outwardly at the center than at both the upper and lower ends along the y direction and recessed more inwardly at the center than at both the upper and lower ends along the x direction.

According to Embodiment 9, the side at the distal end 10c of the sensor cylinder 10 can come closely into direct contact with the cervical or waist part of a subject to be examined along the y direction even when the subject remains not bent forward with its neck or waist curved naturally. Also, the side at the distal end 10c of the sensor cylinder 10 can come into direct contact with the cervical or waist part of the subject along the x direction.

Embodiment 10

As shown in FIG. 18, there may further be provided a sliding handle 12 for an operator slidably moving the carriage 4 in the forward and backward directions (along the z direction) and another sliding handle 13 for an operator slidably moving the carriage 4 in the upward and downward directions (along the Y direction).

The action of correctly setting the side at the distal end of the sensor cylinder 10 to a region of the subject T to be measured will be explained below.

(1) The turning handle 9 is operated to hold the sensor cylinder 10 at the horizontal.

Figure 19:
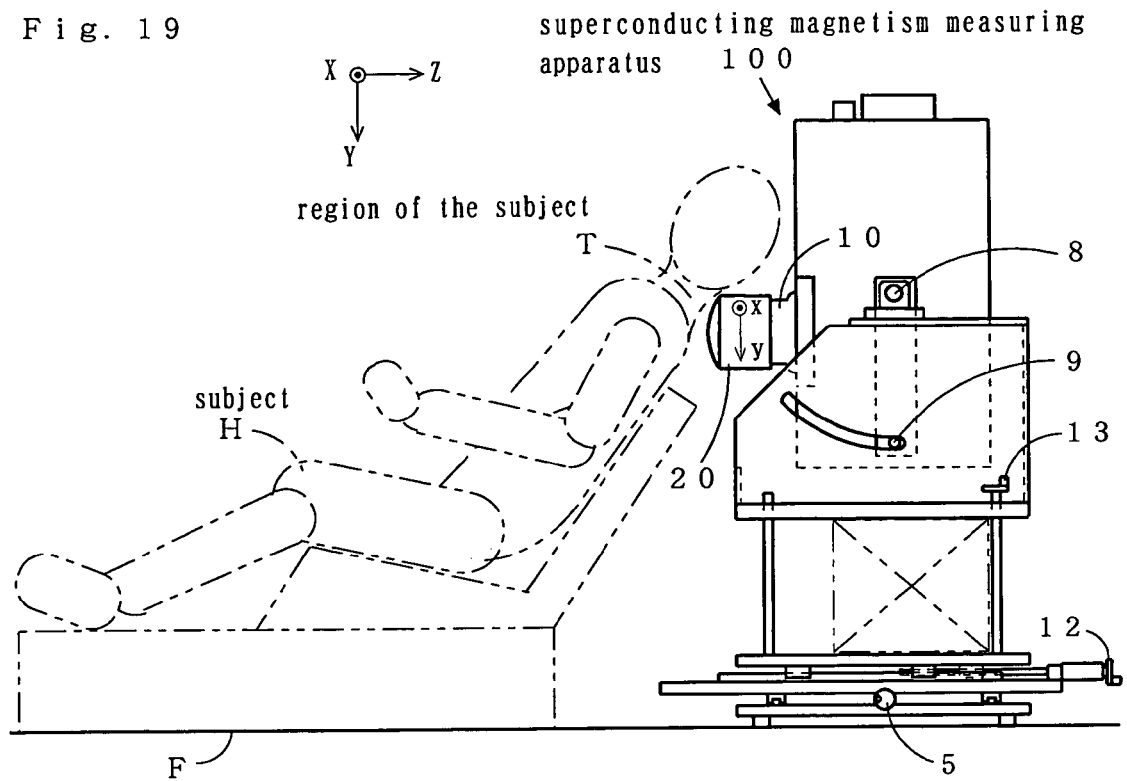
FIG. 19 is an explanatory view showing (the first half of) an action of driving the sensor cylinder of the biomagnetism measuring apparatus of Embodiment 10 to a subject to be examined.

(2) As shown in FIG. 19, both the sliding handles 12 and 13 are operated to move the side at the distal end of the sensor cylinder cover 20 (or the side at the distal end of the sensor cylinder 10 with no use of the cylinder sensor cover 20) so that its upper end comes into direct contact with the upper end of the region of the subject T.

Figure 20:
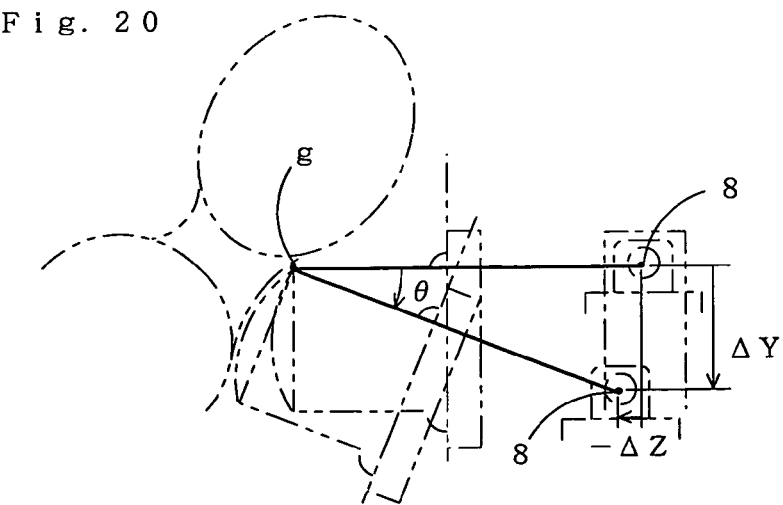
FIG. 20 is an explanatory view showing (the second half of) the action of driving the sensor cylinder of the biomagnetism measuring apparatus of Embodiment 10 to the subject to be examined.

(3) As shown in FIG. 20, the sensor cylinder 10 is turned to modify its angle θ about the center g of its turning or the contact between the upper end of its side at the distal end and the upper end of the region of the subject T until the side at the distal end of the sensor cylinder cover 20 (or the side at the distal end of the sensor cylinder 10 with no use of the cylinder sensor cover 20) is entirely engaged with the region of the subject T to be measured. More specifically, the sensor cylinder 10 is modified in the angle θ by operating the turning handle 9 while the carriage 4 is moved −ΔZ to the front or the rear by operating the sliding hand 12 to the forward or backward and ΔY to the upward or downward by operating the sliding hand 13. Assuming that the distance between the turnable shaft 8 and the upper end of the side at the distal end of the sensor cylinder 10 (at the center g of the turning) which remain held at equal height with the sensor cylinder 10 extended horizontal is Zg, the following relationship will be established, $$\Delta Y = 2 \times Zg \times \sin(\theta/2) \times \cos(\theta/2),$$

$$\Delta Z = 2 \times Zg \times \sin(\theta/2) \times \sin(\theta/2).$$

According to Embodiment 10, the side at the distal end of the sensor cylinder cover 20 (or the side at the distal end of the sensor cylinder 10 with no use of the cylinder sensor cover 20) produces no rubbing movements on the subject to be examined and will hardly annoy the subject by giving an uncomfortable feeling.

Embodiment 11

In case that the width along the y direction of the sensor cylinder 10 is smaller than the length of the region of the subject T to be examined, the following action will be carried out after the setting of the side at the distal end of the sensor cylinder 10 directly to the region of a subject T to be examined similar to that of Embodiment 10.

Figure 21:
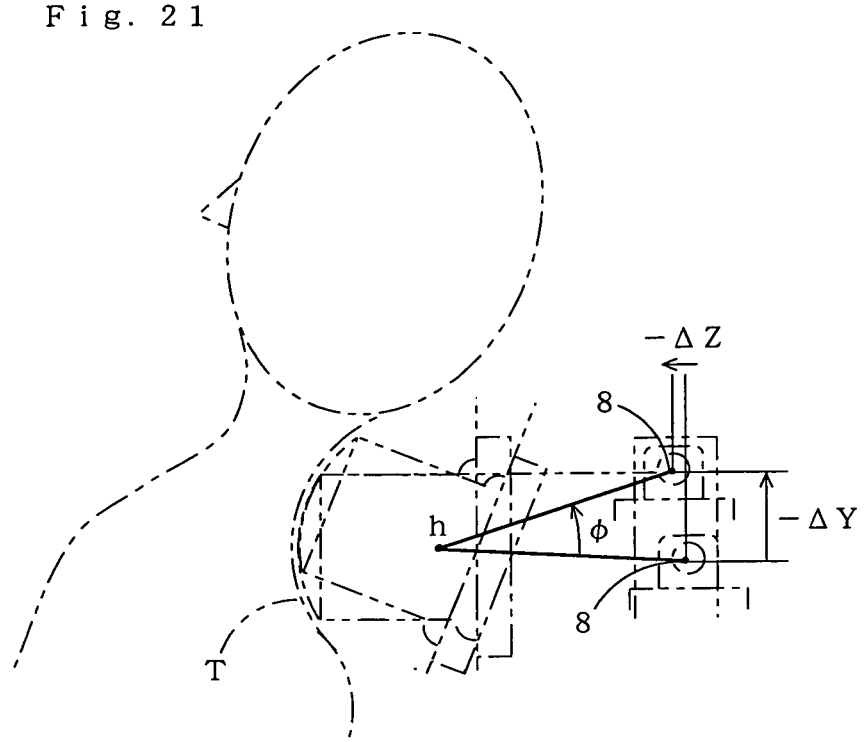
FIG. 21 is an explanatory view showing an action of driving the sensor cylinder of a biomagnetism measuring apparatus according to Embodiment 11 of the present invention.

(4) As shown in FIG. 21, the side at the distal end of the sensor cylinder 10 is turned to modify its angle about the center h of its turning or of its curved shape (or when the shape is an arc, the center of a circle which includes the arc) for moving along the region of the subject T to be examined. More specifically, the sensor cylinder 10 is modified in the angle φ by operating the turning handle 9 while the carriage 4 is moved −ΔZ to the front or the rear by operating the sliding hand 12 to the forward or backward and −ΔY to the upward or downward by operating the sliding hand 13. Assuming that the distance between the tamable shaft 8 and the center h of the turning is Zh with the sensor cylinder 10 turned through the angle φ and extended horizontal as shown in FIG. 21, the following relationship will be established, $$\Delta Y = 2 \times Zh \times \sin(\varphi/2) \times \cos(\varphi/2),$$

$$\Delta Z = 2 \times Zh \times \sin(\varphi/2) \times \sin(\varphi/2).$$

According to Embodiment 11, the side at the distal end of the sensor cylinder 10 can move along the arcuate form of the region of the subject T to be examined.

Embodiment 12

Figure 22:
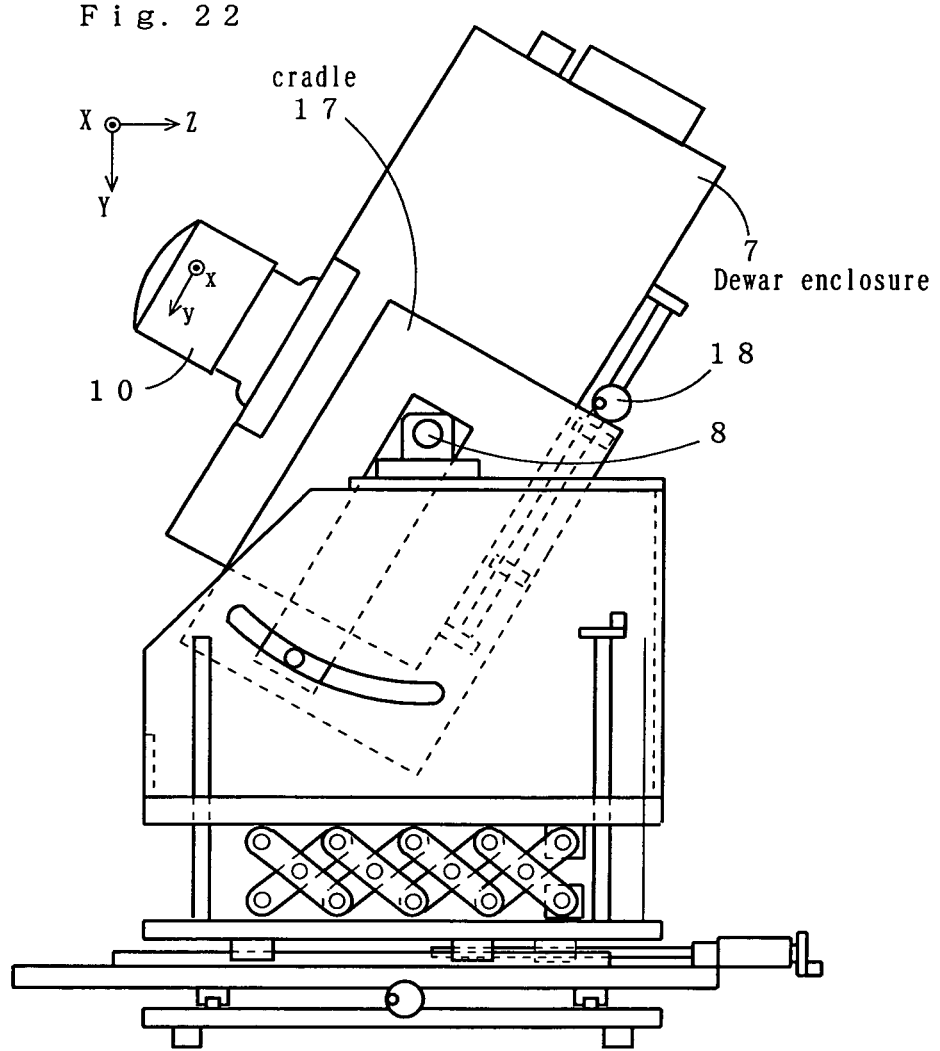
FIG. 22 is a right side view of a biomagnetism measuring apparatus showing Embodiment 12 of the present invention.

As shown in FIG. 22, the Dewar enclosure 7 may be supported by a cradle 17, which is rotatably supported by the turning shaft 8, for movement along the y direction.

By an operator operating the sliding handle 18, the side at the distal end of the sensor cylinder 10 can be moved along the y direction.

Example 1

As shown in FIG. 23, models A, B, C, and D were prepared having a width of 145 mm along the y direction and arranged of an arcuate shape at one side at the distal end of which the projection (the distance at the center projecting outwardly from the upper and lower ends along the y direction) was 5 mm, 10 mm, 20 mm, and 30 mm respectively.

A test was carried out for examining the matching of the models A, B, C, and D with the cervical parts of twenty seven patients who were going to have surgical operations for cervical defects.

As the cervical part of each patient was pictured together with the superconducting magnetism sensors 11 along the x direction by an X-ray photographic camera, the shortest distance from the superconducting magnetism sensors 11 to the cervical part was measured in an X-ray image. The strength of the magnetic field was then calculated from the shortest distance and it was judged that the model of which the magnetic field strength was maximum was the most favorable model.

Consequently, the number of the patients matched maximum with the model A is two, the number of the patients matched maximum with the model B is eleven, the number of the patients matched maximum with the model C is fourteen, and the number of the patients matched maximum with the model D is zero. It is hence proved that the projection of the arcuate shape for measurement of cervical parts is preferably not smaller than 5 mm and not greater than 30 nm.

INDUSTRIAL APPLICABILITY

The present invention is favorable for use as a system for measuring a faint degree of the magnetism generated in the spinal cords or nerves of a human being.

What is claimed is:

1. A superconducting magnetism measuring apparatus, comprising:
   a sensor array of superconducting magnetic sensors aligned in parallel and mounted on an inner surface of one side at the distal end of a sensor cylinder, each one sensor of the sensor array having a distal end, the distal ends of the sensors of the sensor array having a common orientation while being staggered in the y direction;
   wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction.

2. A superconducting magnetism measuring apparatus according to claim 1, wherein
   the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction.

3. A superconducting magnetism measuring apparatus according to claim 2, wherein
   a side at the distal end of the sensor cylinder is curved so as to project outwardly at the center not smaller than 0.5 cm and not greater than 3 cm from both the upper and lower ends along the y direction.

4. A superconducting magnetism measuring apparatus, comprising:
   a sensor array of superconducting magnetic sensors aligned in parallel and mounted on an inner surface of one side at the distal end of a sensor cylinder, each one sensor of the sensor array having a distal end, the distal ends of the sensors of the sensor array having a common orientation while being staggered in the y direction;
   wherein the superconducting magnetic sensors in the sensor array are aligned in both the y direction and the x direction while a side of the sensor cylinder at the distal end of the sensor cylinder is curved so as to project outwardly at the center from both the upper and lower ends along the y direction and to be recessed at the center from both the upper and lower ends along the x direction.

5. A superconducting magnetism measuring apparatus according to any of claims 1 to 4, wherein
the side at the distal end of the sensor cylinder is provided visibly with markers made of a non-magnetic material which diminish passage of X-rays relative to passage through areas adjacent to a marker of said markers.

6. A superconducting magnetism measuring apparatus according to any of claims 1 to 4, further comprising:
an X-ray photographing means for producing X-ray photos of a space along the x direction which includes the side at the distal end of the sensor cylinder.

7. A superconducting magnetism measuring apparatus according to any of claims 1 to 4,
wherein the sensor cylinder is movable along the x direction;
wherein the sensor cylinder is turnable about the axis extending along the x direction;
wherein the sensor cylinder is movable along a horizontal direction extending perpendicular to the x direction; and
wherein the sensor cylinder is movable upwardly and downwardly.

8. A biomagnetism measuring method of the superconducting magnetism measuring apparatus defined in claim 7 comprising the steps of:
holding horizontally the sensor cylinder of the superconducting magnetism measuring apparatus and moving its side at the distal end from the back to a living subject to be measured;
abutting the distal end of a sensor cylinder to a region of a living subject; and
turning a side at the distal end of the sensor cylinder about the contact until the side at the distal end of the sensor cylinder comes entirely into direct contact with the region of the living subject.

9. A biomagnetism measuring method of the superconducting magnetism measuring apparatus defined in claim 7 comprising the steps of:
abutting the distal end of the sensor cylinder to a region of a living subject;
turning the side at the distal end of the sensor cylinder about the center of curvature of the arcuate shape of the side at the distal end of the sensor cylinder; and
moving the side at the distal end of the sensor cylinder along the region of a curved form of the living subject.

10. A superconducting magnetism measuring apparatus, comprising a sensor array of superconducting magnetic sensors aligned and mounted on an inner surface of one side at the distal end of a sensor cylinder,
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction, and
wherein the side at the distal end of the sensor cylinder is provided visibly with markers made of a non-magnetic material which diminish passage of X-rays relative to passage through areas adjacent to a marker of said markers.

11. A superconducting magnetism measuring apparatus, comprising a sensor array of superconducting magnetic sensors aligned and mounted on an inner surface of one side at the distal end of a sensor cylinder,
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction, and
wherein the side at the distal end of the sensor cylinder is provided visibly with markers made of a non-magnetic material which diminish passage of X-rays relative to passage through areas adjacent to a marker of said markers.

12. A superconducting magnetism measuring apparatus, comprising a sensor array of superconducting magnetic sensors aligned and mounted on an inner surface of one side at the distal end of a sensor cylinder,
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction,
wherein the sensor cylinder is substantially 145 mm in the width along the y direction and its side at the distal end is curved so as to project outwardly at the center not smaller than 0.5 cm and not greater than 3 cm from both the upper and lower ends along the y direction, and
wherein the side at the distal end of the sensor cylinder is provided visibly with markers made of a non-magnetic material which diminish passage of X-rays relative to passage through areas adjacent to a marker of said markers.

13. A superconducting magnetism measuring apparatus, comprising a sensor array of superconducting magnetic sensors aligned and mounted on an inner surface of one side at the distal end of a sensor cylinder,
wherein the superconducting magnetic sensors in the sensor array are aligned in both the y direction and the x direction while a side of the sensor cylinder at the distal end of the sensor cylinder is curved so as to project outwardly at the center from both the upper and lower ends along the y direction and to be recessed at the center from both the upper and lower ends along the x direction, and
wherein the side at the distal end of the sensor cylinder is provided visibly with markers made of a non-magnetic material which diminish passage of X-rays relative to passage through areas adjacent to a marker of said markers.

14. A biomagnetism measuring method for a superconducting magnetism measuring apparatus comprising:
- a sensor array of superconducting magnetic sensors aligned and mounted on an inner surface of one side at the distal end of a sensor cylinder;
- wherein the sensor cylinder is movable along an x direction, is turnable about an axis extending along the x direction, is movable along a horizontal direction extending perpendicular to the x direction, and is movable upwardly and downwardly; and
- wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction;
- the method comprising the steps of:
  - holding horizontally the sensor cylinder of the superconducting magnetism measuring apparatus and moving its side at the distal end from the back to a living subject to be measured;
  - abutting the distal end of a sensor cylinder to a region of a living subject; and
  - turning a side at the distal end of the sensor cylinder about the contact until the side at the distal end of the sensor cylinder comes entirely into direct contact with the region of the living subject.

15. A biomagnetism measuring method for a superconducting magnetism measuring apparatus comprising:
- a sensor array of superconducting magnetic sensors aligned and mounted on an inner surface of one side at the distal end of a sensor cylinder;
- wherein the sensor cylinder is movable along an x direction, is turnable about an axis extending along the x direction, is movable along a horizontal direction extending perpendicular to the x direction, and is movable upwardly and downwardly; and
- wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
- wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction, and
- the method comprising the steps of:
  - holding horizontally the sensor cylinder of the superconducting magnetism measuring apparatus and moving its side at the distal end from the back to a living subject to be measured;
  - abutting the distal end of a sensor cylinder to a region of a living subject; and
  - turning a side at the distal end of the sensor cylinder about the contact until the side at the distal end of the sensor cylinder comes entirely into direct contact with the region of the living subject.

16. A biomagnetism measuring method for a superconducting magnetism measuring apparatus comprising:
- a sensor array of superconducting magnetic sensors aligned and mounted on an inner surface of one side at the distal end of a sensor cylinder;
- wherein the sensor cylinder is movable along an x direction, is turnable about an axis extending along the x direction, is movable along a horizontal direction extending perpendicular to the x direction, and is movable upwardly and downwardly; and
- wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
- wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction,
- wherein a side at the distal end of the sensor cylinder is curved so as to project outwardly at the center not smaller than 0.5 cm and not greater than 3 cm from both the upper and lower ends along the y direction, and
- the method comprising the steps of:
  - holding horizontally the sensor cylinder of the superconducting magnetism measuring apparatus and moving its side at the distal end from the back to a living subject to be measured;
  - abutting the distal end of a sensor cylinder to a region of a living subject; and
  - turning a side at the distal end of the sensor cylinder about the contact until the side at the distal end of the sensor cylinder comes entirely into direct contact with the region of the living subject.

17. A biomagnetism measuring method for a superconducting magnetism measuring apparatus comprising:
- a sensor array of superconducting magnetic sensors aligned and mounted on an inner surface of one side at the distal end of a sensor cylinder;
- wherein the sensor cylinder is movable along an x direction, is turnable about an axis extending along the x direction, is movable along a horizontal direction extending perpendicular to the x direction, and is movable upwardly and downwardly; and
- wherein the superconducting magnetic sensors in the sensor array are aligned in both the y direction and the x direction while a side of the sensor cylinder at the distal end of the sensor cylinder is curved so as to project outwardly at the center from both the upper and lower ends along the y direction and to be recessed at the center from both the upper and lower ends along the x direction, and
- the method comprising the steps of:
  - holding horizontally the sensor cylinder of the superconducting magnetism measuring apparatus and moving its side at the distal end from the back to a living subject to be measured;
  - abutting the distal end of a sensor cylinder to a region of a living subject; and
  - turning a side at the distal end of the sensor cylinder about the contact until the side at the distal end of the sensor cylinder comes entirely into direct contact with the region of the living subject.

18. A biomagnetism measuring method for a superconducting magnetism measuring apparatus comprising:
a sensor array of superconducting magnetic sensors aligned and mounted on an inner surface of one side at the distal end of a sensor cylinder;
wherein the sensor cylinder is movable along an x direction, is turnable about an axis extending along the x direction, is movable along a horizontal direction extending perpendicular to the x direction, and is movable upwardly and downwardly; and
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction;
the method comprising the steps of:
abutting the distal end of the sensor cylinder to a region of a living subject;
turning the side at the distal end of the sensor cylinder about the center of curvature of the arcuate shape of the side at the distal end of the sensor cylinder; and
moving the side at the distal end of the sensor cylinder along the region of a curved form of the living subject.

19. A biomagnetism measuring method for a superconducting magnetism measuring apparatus comprising:
a sensor array of superconducting magnetic sensors aligned and mounted on an inner surface of one side at the distal end of a sensor cylinder;
wherein the sensor cylinder is movable along an x direction, is turnable about an axis extending along the x direction, is movable along a horizontal direction extending perpendicular to the x direction, and is movable upwardly and downwardly; and
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction, and
the method comprising the steps of:
abutting the distal end of the sensor cylinder to a region of a living subject;
turning the side at the distal end of the sensor cylinder about the center of curvature of the arcuate shape of the side at the distal end of the sensor cylinder; and
moving the side at the distal end of the sensor cylinder along the region of a curved form of the living subject.

20. A biomagnetism measuring method for a superconducting magnetism measuring apparatus comprising:
a sensor array of superconducting magnetic sensors aligned and mounted on an inner surface of one side at the distal end of a sensor cylinder;
wherein the sensor cylinder is movable along an x direction, is turnable about an axis extending along the x direction, is movable along a horizontal direction extending perpendicular to the x direction, and is movable upwardly and downwardly; and
wherein the superconducting magnetic sensors in the sensor array are aligned in the y direction and the x direction while a side of the sensor cylinder at the distal end of the sensor cylinder is curved so as to project outwardly at the center from both the upper and lower ends along the y direction but not curved along the x direction,
wherein the sensor cylinder is arranged of a four-sided cylindrical shape having a width along the y direction of not smaller than 5 cm and not greater than 20 cm and a width along the x direction of not smaller than 5 cm and not greater than 20 cm and its side at the distal end is curved so as to project outwardly at the center not smaller than 0.5 cm and not greater than 4 cm from both the upper and lower ends along the y direction,
wherein a side at the distal end of the sensor cylinder is curved so as to project outwardly at the center not smaller than 0.5 cm and not greater than 3 cm from both the upper and lower ends along the y direction, and
the method comprising the steps of:
abutting the distal end of the sensor cylinder to a region of a living subject;
turning the side at the distal end of the sensor cylinder about the center of curvature of the arcuate shape of the side at the distal end of the sensor cylinder; and
moving the side at the distal end of the sensor cylinder along the region of a curved form of the living subject.

21. A biomagnetism measuring method for a superconducting magnetism measuring apparatus comprising:
a sensor array of superconducting magnetic sensors aligned and mounted on an inner surface of one side at the distal end of a sensor cylinder;
wherein the sensor cylinder is movable along an x direction, is turnable about an axis extending along the x direction, is movable along a horizontal direction extending perpendicular to the x direction, and is movable upwardly and downwardly; and
wherein the superconducting magnetic sensors in the sensor array are aligned in both the y direction and the x direction while a side of the sensor cylinder at the distal end of the sensor cylinder is curved so as to project outwardly at the center from both the upper and lower ends along the y direction and to be recessed at the center from both the upper and lower ends along the x direction, and
the method comprising the steps of:
abutting the distal end of the sensor cylinder to a region of a living subject;
turning the side at the distal end of the sensor cylinder about the center of curvature of the arcuate shape of the side at the distal end of the sensor cylinder; and
moving the side at the distal end of the sensor cylinder along the region of a curved form of the living subject.

* * * * *